United States Patent [19]

Aoki et al.

[11] Patent Number: 4,737,035
[45] Date of Patent: Apr. 12, 1988

[54] METHOD OF AND APPARATUS FOR MEASURING DAMPENING WATER FOR PRINTING MACHINE

[75] Inventors: Kenichi Aoki, Tanashi; Asaya Ohta, Niiza, both of Japan

[73] Assignee: Sumitomo Heavy Industries, Ltd., Tokyo, Japan

[21] Appl. No.: 65,646

[22] Filed: Jun. 24, 1987

Related U.S. Application Data

[63] Continuation of Ser. No. 610,738, May 16, 1984, abandoned.

[30] Foreign Application Priority Data

May 17, 1983 [JP] Japan ................................. 58-85135
Mar. 23, 1984 [JP] Japan ................................. 59-55377

[51] Int. Cl.⁴ ........................ G01N 21/47; G01N 21/55
[52] U.S. Cl. ............................ 356/445; 101/DIG. 24; 356/446
[58] Field of Search ................................ 356/445–448

[56] References Cited

U.S. PATENT DOCUMENTS

| | | | |
|---|---|---|---|
| 3,870,884 | 3/1975 | Williams | 250/339 |
| 3,960,077 | 6/1976 | Aylett | 356/448 X |
| 4,052,937 | 10/1977 | Lawson et al. | 356/445 X |
| 4,072,426 | 2/1978 | Horn | 356/446 X |
| 4,227,809 | 10/1980 | Satoh et al. | 356/446 X |
| 4,525,630 | 6/1985 | Chapman | 356/446 X |

FOREIGN PATENT DOCUMENTS 3134264 3/1983 Fed. Rep. of Germany ... 101/DIG. 24
2104478 8/1970 France .

Primary Examiner—Vincent P. McGraw
Attorney, Agent, or Firm—Armstrong, Nikaido, Marmelstein & Kubovcik

[57] ABSTRACT

In order to effect an optimum control of the rate of supply of dampening water to the surface of a plate carried by a plate cylinder of a printing machine, particularly an offset press, the amount of dampening water on the surface of the plate or the surface of a roller through which the dampening water is supplied to the plate or the surface of an additional roller contacting with the water supplying roller is measured optically. The measurement is conducted by applying parallel rays of light to the objective surface at a predetermined angle of incidence, and measuring the intensity of the mirror-reflected light reflected by the surface at the same angle as the incident light. By measuring the mirror-reflected light insteadly of diffused light, it becomes possible to enhance the accuracy of the measurement and to widen the range of measurement.

5 Claims, 9 Drawing Sheets

METHOD OF AND APPARATUS FOR MEASURING DAMPENING WATER FOR PRINTING MACHINE

This application is a continuation of application Ser. No. 610,738 filed May 16, 1986, now abandoned.

BACKGROUND OF THE INVENTION

The present invention relates to a method of and apparatus for measuring dampening water for a printing machine. More particularly, the invention is concerned with a method of and apparatus for optically measuring the amount of dampening water on the surface of a plate attached to a plate cylinder of an offset press for the purpose of controlling the rate of supply of the dampening water to the plate surface.

Hitherto, various methods have been proposed for measuring the amount of dampening water on the plate surface. For instance, it is known to measure the amount of the dampening water through measuring the amount of absorption of infrared rays by the dampening water. According to another known method, the amount of dampening water is detected through measurement of the humidity around the plate surface. According to still another known method, the amount of dampening water is deterninined by measuring the electric resistance of the water film on a dampening water roller. These methods, however, have not been put into practical use yet.

French Patent No. 2,104,478 discloses a method which makes use of a phenomenon that, when parallel rays of light are applied to a thin film of water, the intensity of the reflected light in relation to the reflecting angle varies depending on the thickness of the thin water film. Namely, the above-mentioned French patent proposes to measure the amount of the dampening water by applying light to the plate surface and measuring the quantity of the light reflected from the plate surface. This measuring method proposed by the above-mentioned French patent involves the following problems. The apparatus for measuring the light reflected by the plate surface has a light-receiving element which is disposed in the angular region of, for example, 60° to 80° which is smaller than the angle for mirror-reflection which is equivalent to the incident angle of the light applied to the plate surface; so as to receive and measure the diffused light. Therefore, the light-receiving element can receive only small quantity of reflected light and, hence, often suffers a large error in the measurement. Therefore, as will be fully explained later, the quantity of the received light cannot be determined by a single-valued function in relation to the quantity of light received. Furthermore, since the angle of incidence of the light is as large as 80° to 85°, the incoming light is interferred by the roughness of the plate surface so that the range of measurement is limited undesirably.

SUMMARY OF THE INVENTION

Accordingly, an object of the invention is to provide a method of and apparatus for measuring the dampening water for printing machine, making use of the light reflected from the plate surface, improved to provide a greater range of measurement and to reduce the measuring error, thereby to overcome the above-described problems of the prior art.

To this end, according to one aspect of the invention, there is provided a method of measuring dampening water on a printing machine comprising: applying, at a predetermined angle of incidence, parallel rays of light to the surface of a plate on the printing machine or to the surface of one of rollers of a water supply system through which the dampening water is supplied to the plate surface or to the surface of a separate roller contacting one of rollers of the water supply system; and measuring the intensity of the mirror-reflected light from the surface.

According to another aspect of the invention, there is provided an apparatus for measuring dampening water on a printing machine comprising: a light applying means for applying, at a predetermined angle of incidence, parallel rays of light to the surface of a plate on the printing manine or to the surface of one of rollers of a water supply system for supplying the dampening water to the plate or to the surface of a separate roller contacting the one of rollers of the water supply system; and a sensor adapted to receive the mirror-reflected light reflected by the surface at an angle same as the incident angle and to measure the intensity of the mirror-reflected light.

The term "mirror-reflected light" in this specification is not used in a microscopic sense but is used to mean the light reflected by a flat surface such as of a metal plate.

In a preferred form of the invention of this application, the intensity of the diffusion-reflected light is measured in addition to the intensity of the mirror-reflected light, and the amount of the dampening water is determined taking into account the ratio between both light intensities. By so doing, it is possible to compensate for any influence of output fluctuation of the light source.

The mirror-reflected light may be measured on any surface provided that the surface carries a dampening water. When the mirror-reflected light from the plate surface is to be measured directly, it is necessary to detect the notches formed in the plate cylinder for securing the plate and to discriminate the printing area and non-printing area on the plate surface from each other, in order to optimumly determine the measuring point on the plate surface. In addition, since different plates have different states of roughness of grains of the plate material, it is necessary to effect a correction of the maasured value at each time the plate is changed, in order to eliminate any error attributable to the difference of the state of the roughness of grains. As an alternative measure, it is possible to use a dampening water measuring roller which contacts one of the rollers, particularly the dampener form roller, of the system for supplying water to the plate surface. In such a case, the surface of the dampening water measuring roller is grained in same manner as the non-printing area of the plate, and the mirror-reflected light from the surface of this roller is measured. According to this method, it is possible to select any point on the roller surface as the reflecting point. In addition, the measuring error can be supressed advantageously because the state of roughness of grains on the dampening water measuring roller is never changed even if the plate is changed. It is possible to use one of existing rollers of the water supplying system as the dampening water measuring roller or a separate roller contacting one of the existing rollers may be provided as the dampening water measuring roller.

The above and other objects, features and advantages of the invention will become clear from the following description of the preferred embodiments taken in conjunction with the accompanying drawings.

DESCRIPTION OF THE PREFERRED EMBODIMENTS

Before turning to the detailed description of the invention, an explanation will be made as to the relationship which exists between the amount of water held on the measured surface and the directivity of the reflected light.

Figure 1:
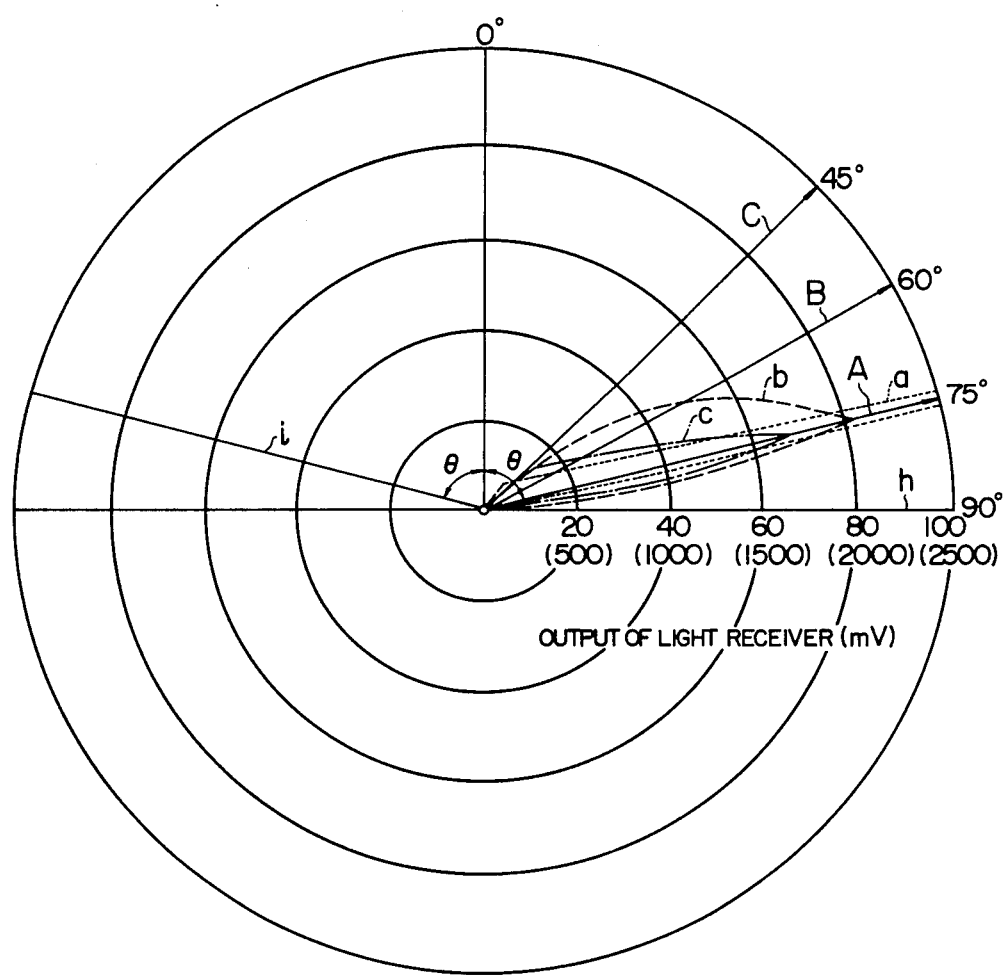
FIG. 1 is a diagram showing the relationship between the amount of water on the measured surface and the directivity of the reflected light.
Figure 2:
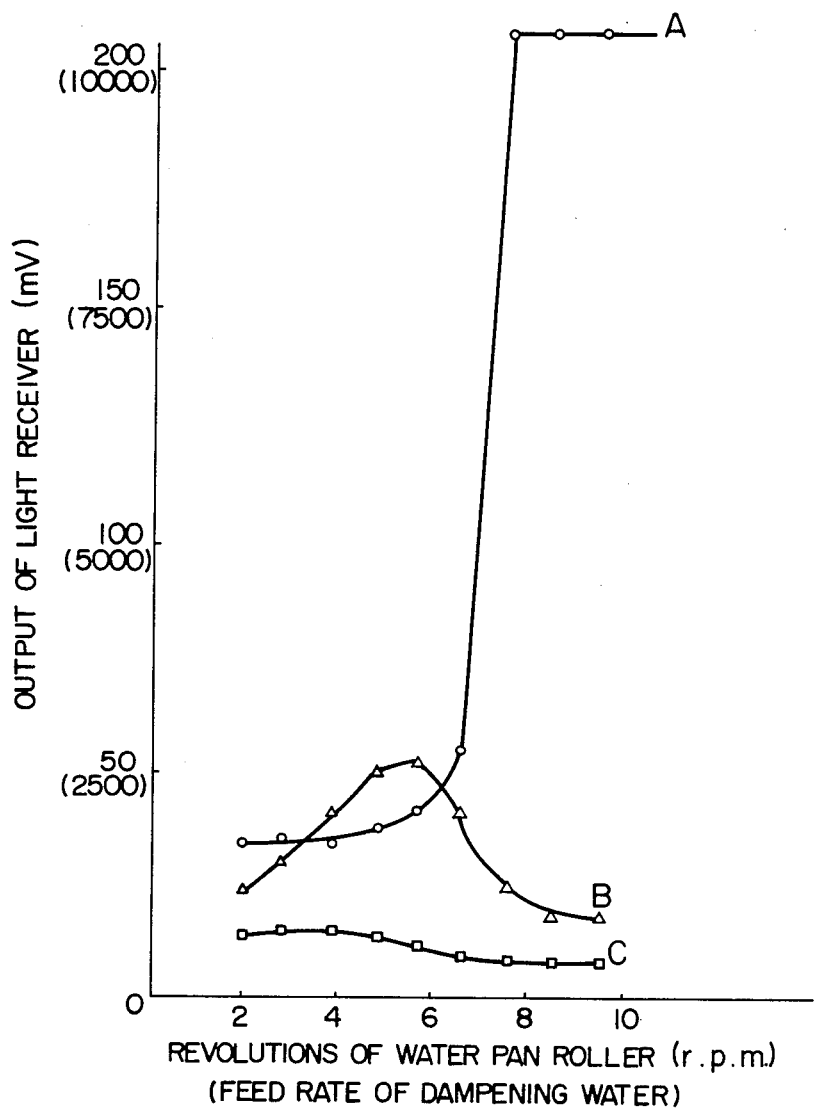
FIG. 2 is a diagram showing the relationship between the amount of water on the measured surface and the amount of received reflected light.

FIG. 1 is a diagram showing the relationship between the amount of water held by a measured surface and the directivity of the intensity of the light reflected by the measured surface. A light i impinges upon the measured surface h at an incident angle of $\theta$. Broken lines a, b and c represent, respectively, the directivities of the light reflected by the measured surface h when the latter holds a large, medium and small amounts of water. In this FIG., an arrow A represents the direction of the mirror-reflected light, while arrows B and C represent two different diffused lights. More specifically, the diagram shown in FIG. 1 has been obtained by plotting, on a polar coordinate, the values in the graph of FIG. 2 showing the result of an experiment conducted to seek for the relationship between the rate of supply of the dampening water and the intensity of the reflected light. The intensity of the mirror-reflected light, which is extremely large as compared with those of the diffused lights, is represented by values in the parentheses. As will be seen from this Figure, the diffusion of light reflected by the measured surface is large when the amount of water is small, and the diffusion becomes weaker, i.e. the reflection characteristics approach the mirror reflection.

FIG. 2 is the graph which shows how the intensities of reflected lights in directions of arrows A, B and C (output voltages of light receiving element) are changed in accordance with the change in revolutions of the water pan roller, i.e. the rate of supply of the dampening water to the plate. As will be seen from this FIG., the intensity of the light in the direction of arrow A (mirror-reflected light) saturates when the measured surface carries a large amount of water.

The reflected light in the direction of the arrow B is the diffused light in the angular range near the angle of the mirror reflection. The intensity of this light increases as the amount of water on the measured surface is increased and, after making a peak, decreased as the water amount is further increased. The known method explained before makes use of this characteristic. In this case, the quantity of received light is expressed as a two-valued function of the amount of water held by the measured surface. The reflected light in the direction of the arrow C is a diffused light in an angular range which is far from the angle of the mirror reflection. The quantity of this light is decreased as the amount of water is increased. As in the case of FIG. 1, the intensity of the reflected light (output voltage of light-receiving element) in the direction of the arrow A is represented by the numerical values in the parentheses.

From these facts, it is understood that the measurement of the mirror-reflected light is preferred for attaining a high sensitivity of the measuring apparatus and minimizing the measurement error. Factors affecting the accuracy of measurement, such as the angle of incidence, roughness of the measured surface and the measurable range are considered as follows.

Figure 3:
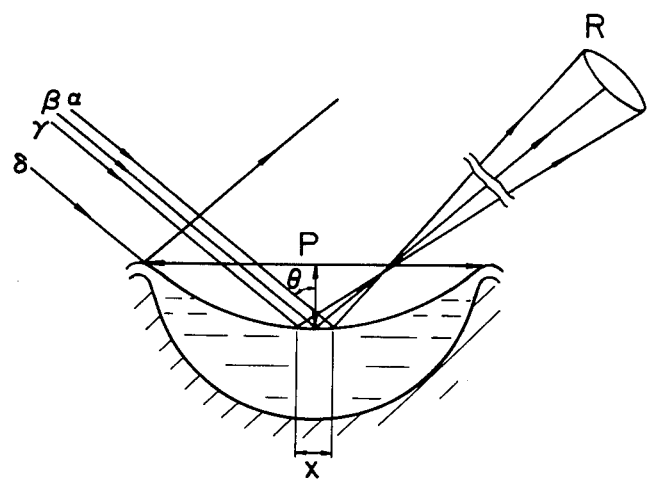
FIG. 3 is an enlarged sectional view of a part of the measured surface, explanatory of the relationship between the incident light coming into the measured surface and the reflected light emerging from the measured surface.

Referring to FIG. 3, parallel rays of light are applied to one of the grains on the measured surface. A light-receiving element R is disposed at a position where it can receive the mirror-reflected light from the measured surface. The light received by the light-receiving element R can be sorted into two groups: namely, the ray 6 impinging upon the crest of the grain and the rays $\alpha$, $\beta$ and $\gamma$ impinging upon the valley of the water surface which assumes a form of a part of a sphere due to the surface tension. The curvature of the water surface, therefore, is rather gentle, while the crests of the grain projects steeply. It is, therefore, considered that the most part of rays of light received by the light receiving element R are reflected at the valley portion of the water surface. More specifically, the light-receiving element R receives rays reflected from the portion of the water surface within a range marked as X in FIG. 3. The range X will be increased as the radius of curvature of the water surface is increased. If the amount of dampening water on the measured surface is increased, the depression of the water surface becomes smaller, i.e. the radius of curvature is increased, so that the range X is widened to increase the amount of quantity of the light received by the light-receiving element R. These understandings lead to a conclusion that a too large incidence angle $\theta$ will decrease the measurable range because rays $\alpha$ and $\gamma$ to impinge upon the ends of the range X are interrupted by the edges of the concavity of the measured surface. The energy reflectivity on the water surface and, therefore, the energy received by the light-receiving element, becomes greater as the angle of incidence gets greater. The incidence angle $\theta$, therefore, should be as large as possible within the range free from the influence of the concavity of the measured surface.

The dampening water measuring apparatus of the invention is composed of a sensor section and a processing section. The sensor section measures the reflection directivity of the measured surface and is constituted by a sensor unit which includes a light source and a light-receiving device, while the processing section makes a computation to determine the value corresponding to the amount of water held by the measured surface, in accordance with the signal from the sensor section.

The light source is preferably constituted by a laser device which produces a light of high luminance and resembling a monochromatic light. The light source is arranged to apply parallel rays of light to the measured surface. On the other hand, the light-receiving device is composed of a photo-electric conversion element such as silicon photodiode and a photo-electric conversion circuit. Preferably, a first light receiving device for receiving the mirror-reflected light and a second light-receiving device for receiving diffused light are provided. By detecting the ratio between the intensity of the mirror-reflected light detected by the first light-receiving device and the intensity of the diffused light detected by the second light-receiving element, it is possible to compensate for any influence of output fluctuation of the light source.

Preferred embodiments of the invention will be described hereinunder.

Figure 4:
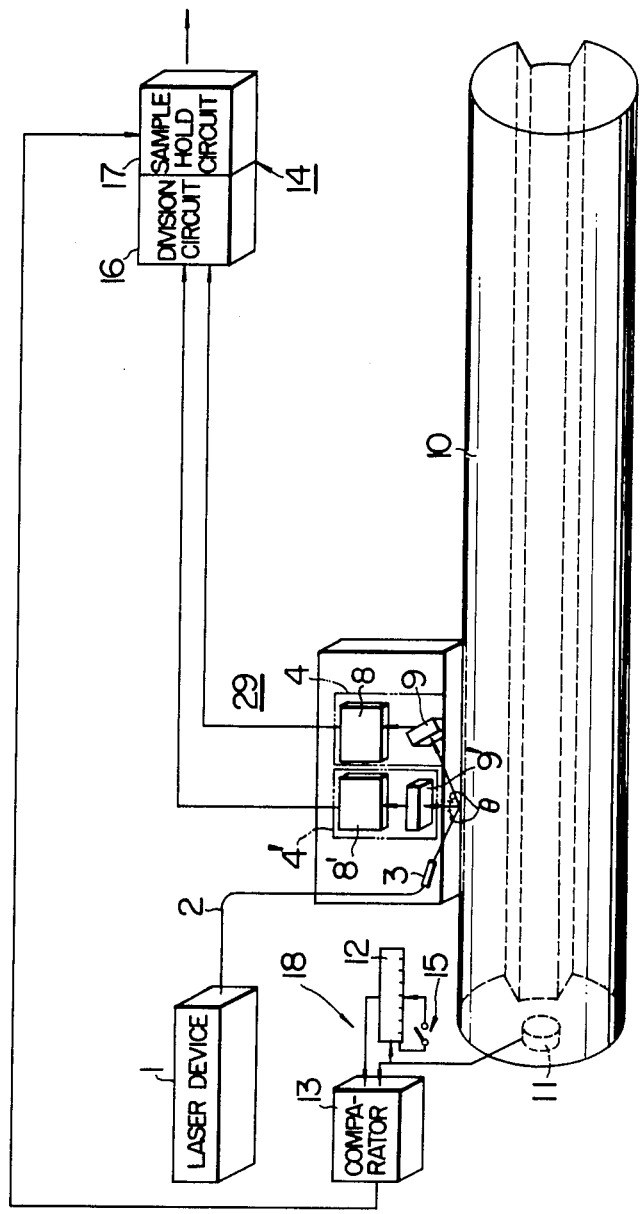
FIG. 4 is a schematic illustration of an embodiment of the invention which is adapted to directly measure the dampening water on the plate surface.

FIG. 4 shows a first embodiment of the invention in which the amount of the water held by the surface of the plate on the plate cylinder is directly measured.

In this embodiment, the sensor section has a helium neon laser device 1 having an output of 0.5 mW. The light beam from this laser device 1 is introduced through an optical fiber 2 to a collimeter 3 attached to a sensor 29 which is adapted to be reciprocatingly driven by a driving device (not shown) along a path above the plate cylinder 10 in the axial direction of the latter. The light beam coming out of the optical fiber 2 impinges upon the plate surface at such an incident angle that the angle $\theta$ formed between the line of the incident light and the line normal to the plate surface is about 75°.

Figure 5:
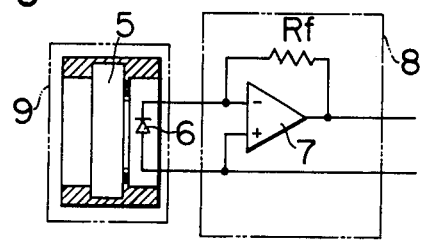
FIG. 5 is a schematic illustration of a photosensor incorporated in the embodiment shown in FIG. 4, with the photoelectric converting section thereof shown in the form of a circuit diagram.

The sensors 29 has light-receiving devices 4 and 4' which are adapted to receive, respectively, the mirror-reflected light reflected at the angle of $\theta$ and the diffused light reflected at the reflection angle of 0°. As shown in FIG. 5, the light-receiving device 4 or 4' is composed of a photo-detecting section 9 or 9' having an interference filter 5, e.g. IF-W type interference filter produced by Nippon Shinku Kogaku K.K., capable of transmitting only the laser light component of wavelength around 633 mm and a silicon photodiode 6 of 20 mm dia., and a photoelectric conversion circuit 8 or 8' constituted by an operation amplifier 7 of MOS FET input type having a small level of input bias current.

A synchronizing signal generating section 18 has an encoder 11 attached to the plate cylinder 10, a detecting position register 12 and a comparator 13 adapted to receive signals from the encoder 11 and the register 12. The comparator 13 produces a synchronizing signal and delivers the same to the processing section 14. A reference numeral 15 designates a detecting position setting switch.

The processing section 14 is composed of a division circuit 16 and a sample and hold circuit 17. The division circuit 16 performs a divisional computation to determine the ratio of the intensity of mirror-reflected light to the intensity of the diffused light, and samples the result of the division in accordance with the synchronizing signal. The computation of the light intensity ratio and the sampling of the same are made for the following reason. The value of this ratio is varied solely by the fluctuation of the amount of water on the plate surface, and the value of the ratio is free from any fluctuation of the reflected light intensity due to a change in the light intensity of the light source. It is, therefore, possible to eliminate any unfavourable effect which may be caused any disturbance or noise.

Figure 6:
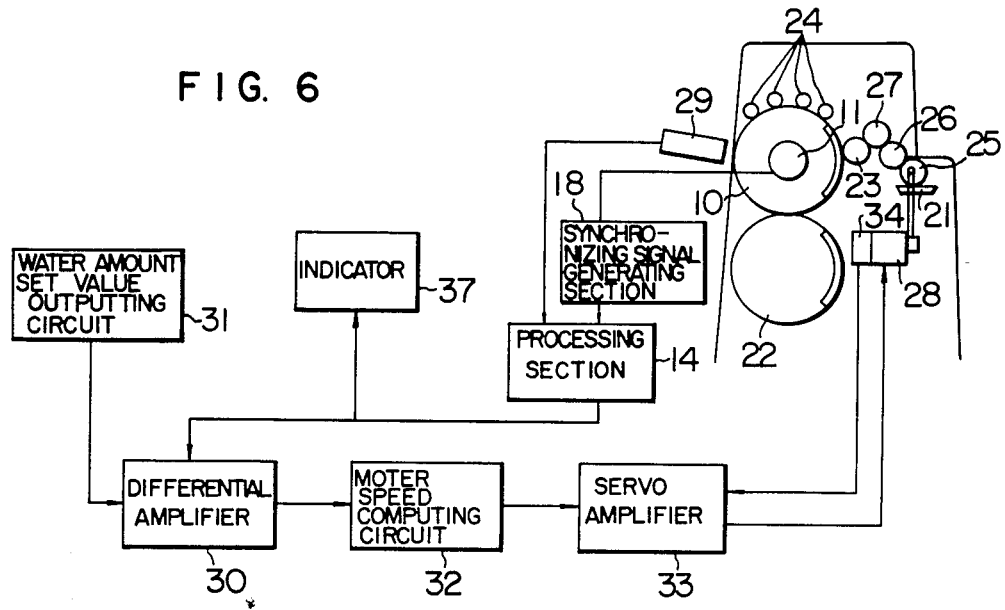
FIG. 6 is a block diagram of a water supply control system making use of the embodiment of the dampening water measuring apparatus shown in FIG. 4.

FIG. 6 shows a dampening water control system making use of the dampening water measuring apparatus as shown in FIG. 4. In this Figure, a reference numeral 10 denotes a plate cylinder, 22 denotes a rubber cylinder, 23 denotes a dampener form roller and 24 denotes ink rollers. The dampening water 21 is transferred from a water pan roller 25 through water supply rollers 26 and 27 to the dampener form roller 23 and is applied by the same to the plate surface. The water pan roller 25 is driven by a water supply motor 28.

Figure 7:
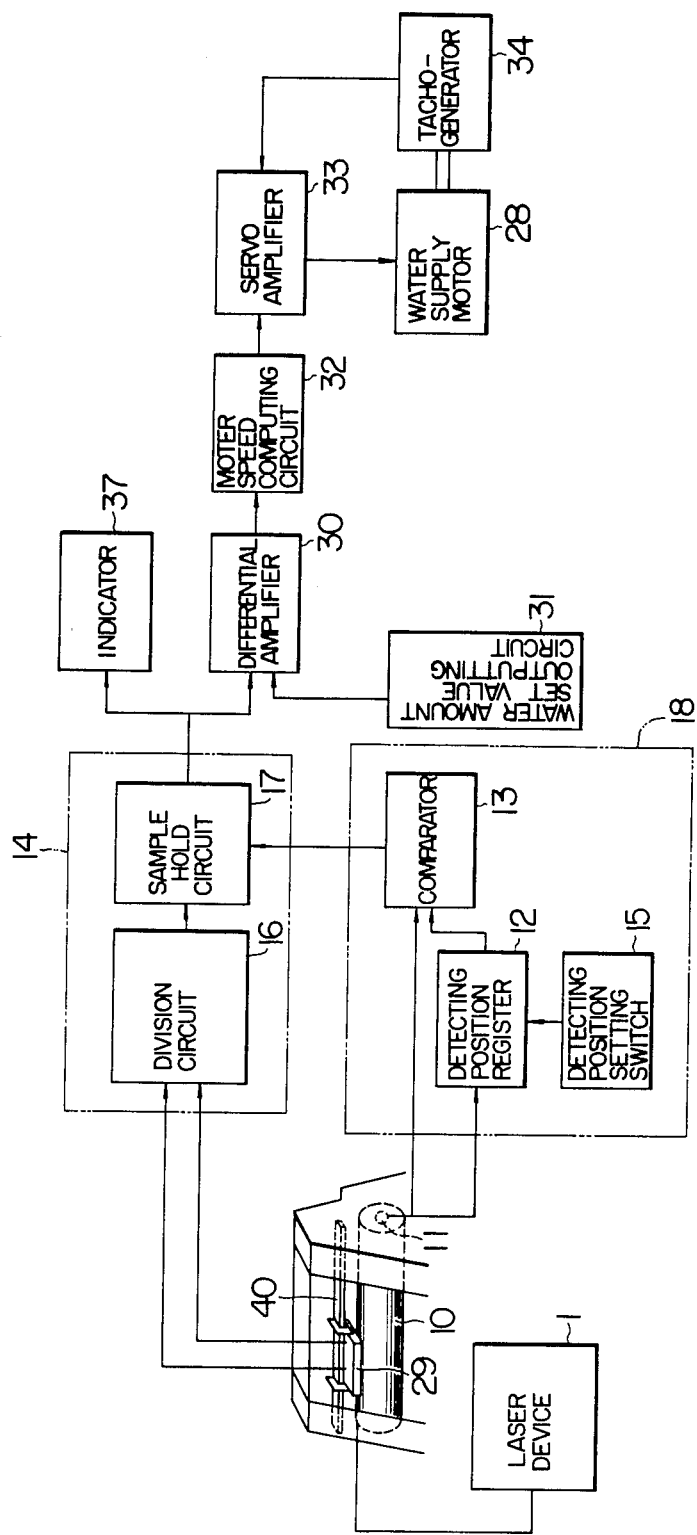
FIG. 7 is a block diagram similar to that shown in FIG. 6 but showing a part of the system in more detail.

As shown in FIG. 7, the sensor 29 is adapted to be moved reciprocatingly in the axial direction of the plate cylinder 10. The processing section 14 picks up, through the synchronizing signal generating section 18, the output signal from the position detecting encoder 11 attached to the plate cylinder 10. The processing section 14 receives also the signal from the sensor 29 and delivers signals representing the measured value to a differential amplifier 30 and an indicator 37.

The differential amplifier 30 compares the set value inputted from a water amount set value outputting circuit 31 with the measured value derived from the processing section 14 and produces a signal representing the difference therebetween. This signal is then delivered to a motor speed computing circuit 32. Upon receipt of the signal from the differential amplifier 30, the motor speed computing circuit 32 delivers an operation signal to the water supply motor 28 through a servo amplifier 33, thereby actuating the motor 28. The speed of the motor 28 is fed back by means of a tachogenerator 34.

The measurement of the amount of water on the plate surface is conducted in accordance with the following process. The sensor 29 is moved along a rail 40 shown in FIG. 7 to a position where it opposes to the non-printing area of the plate on the plate cylinder 10. After determination of the measuring point in the nonprinting area, the sensor 29 is fixed and the detecting position in the circumferential direction of the plate is delivered through the detecting position memory switch 15 to the detection position register 12 so as to be stored in the latter. During measuring, the comparator 13 compares the output of the encoder 11, i.e. the current position of the sensor on the plate cylinder, and the value stored in the detecting position register 12, and delivers a synchronizing signal to the sample and hold circuit 17 in the processing section 14 when output of the encoder has become equal to the value in the register 12, i.e. when the plate has been rotated to the predetermined position for detection. The sample and hold circuit 17 holds the output of the division circuit until the next synchronizing signal is received.

Then, the amount of the water on the plate surface is regulated by controlling the rotation speed of the water supply motor 28 in accordance with the measured value of the water amount and a reference value which is determined beforehand. The measurement and control of the water amount are conducted in both of the actual printing and test printing prior to the actual printing. In the described embodiment, the S/N ratio (signal-to-noise ratio) is improved by the use of the filter 5 having a wavelength selectivity. In addition, the light-receiving section has a size sufficiently large as compared with the diameter of the incident light. For these reasons, a certain degree of allowance is permitted in regard to the positional relationship between the plate and the sensor. Namely, a slight offset of the optic axis on the light-receiving section becomes permissible. It is also to be noted that the collimeter 3 as well as the optical fiber 2 may be omitted if the laser device 1 can emit parallel rays of light of high degree of parallelism to be directly applied to the plate surface.

In the described embodiment, it is necessary to detect the notch in the plate cylinder for securing the plate and to discriminate the non-printing area and the printing area of the plate surface from each other, in order to adequately determine a measuring point. In addition, since different plates have different degrees of roughness of grains, it is necessary to correct the measured value at each time the plate is changed, in order to eliminate error which may be caused by the difference of degree of grain roughness. These problems, however, can be overcome by the second embodiment of the invention in which, insteadly of directly measuring the amount of water on the plate surface, the measurement is made for the amount of water held on the surface of a dampening water measuring roller which is prepared separately to have a surface grained in same manner as the non-printing area of the plate. The dampening water measuring roller is held in contact with one of the rollers in the water supplying system for supplying the plate surface with dampening water or, alternatively, one of the rollers of the water supplying system is used as the dampening water measuring roller. In such a case, the above-mentioned one of rollers is made to have a surface which is grained in same manner as the non-printing area of the plate. The amount of water held by the surface of the measuring roller is a function of the rate of supply of the dampening water to the plate surface. Therefore, it is possible to detect indirectly the amount of water on the plate surface, by measuring the amount of water on the surface of the measuring roller.

Figure 8:
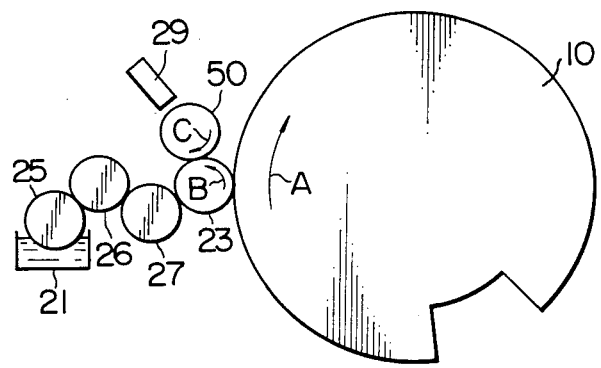
FIG. 8 is a schematic illustration of roller arrangement in another embodiment of the invention, in which a separate roller contacting one of existing rollers of the dampening water supply system is used as the dampening water measuring roller.

FIG. 8 shows a roller arrangement in an embodiment in which the measuring roller is held in contact with the dampener form roller of the water supplying system. The water supplying system includes a water pan 21, water pan roller 25, water transfer rollers 26, 27 and the dampener form roller 23 from which the water is supplied to the plate 10. This roller arrangement of the water supplying system itself is known per se.

The dampener form roller 23 is held in contact with a dampening water measuring roller 50 which has a surface grained equally to the surface of the non printing area of the plate, i.e. processed to have the same surface condition as the plate surface. The dampening water measuring roller 50 is adapted to be rotated simultaneously with the rotation of the dampener form roller 23. This embodiment has the sensor 29 for measuring the amount of dampening water. This sensor is materially identical to that of the preceding embodiment explained in connection with FIG. 4.

The embodiment employing the above-mentioned dampening water measuring roller 50 will be explained hereinunder with reference to FIG. 9.

The beam emitted from the helium neon laser device 1 of 0.5 mW output is introduced through the optical fiber 2 to the collimeter 3 mounted on the sensor 29 which is adapted to be reciprocatingly driven by a driving means (not shown) along a path above the peripheral surface of the measuring roller 50 in the axial direction of the latter. The light beam coming out of the collimeter 3 impinges upon the surface of the measuring roller at an incident angle $\theta$ of about 75° to the line normal to the roller surface. As in the case of the embodiment shown in FIG. 4, the sensor 29 has two light-receiving devices 4 and 4' which are adapted to receive, respectively, the mirror-reflected light reflected at the angle $\theta$ and the difused light reflected at a reflection angle of 0°. The constructions of other major sections such as the sychronizing signal generating section 18 and the processing section 14 are materially identical to those of the embodiment shown in FIG. 4.

Figure 9:
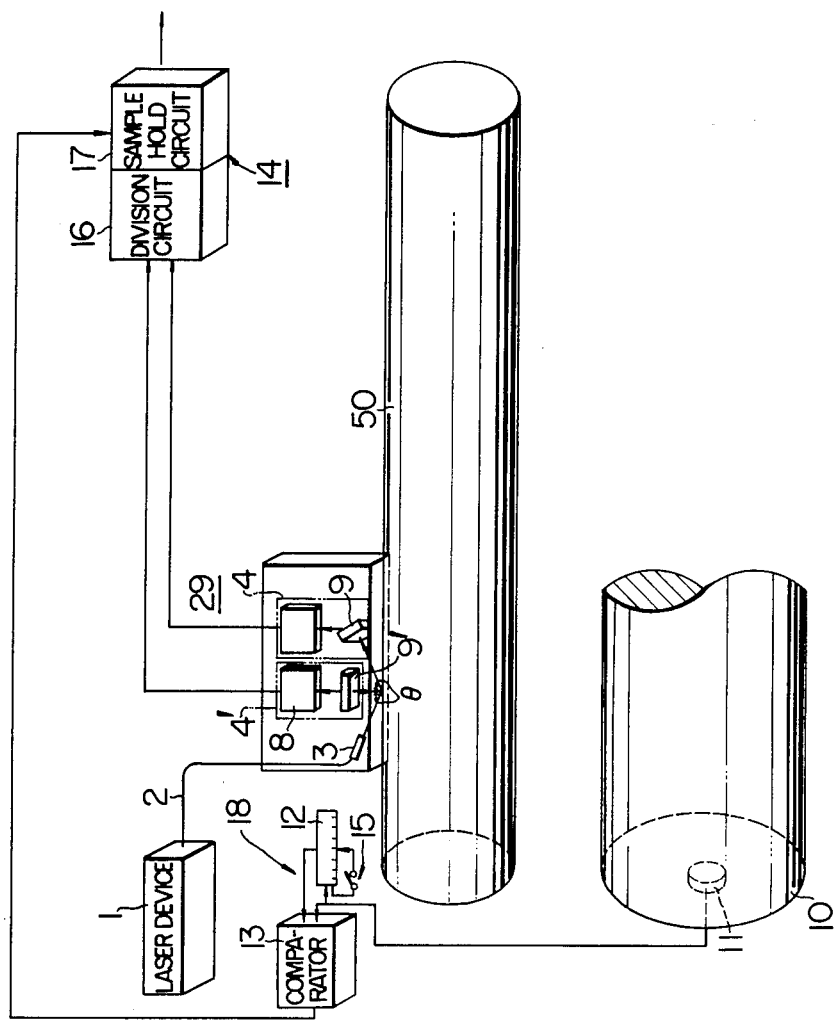
FIG. 9 is a schematic illustration of another embodiment which is adapted to measure the dampening water on the separate dampening water measuring roller shown in FIG. 8.
Figure 10:
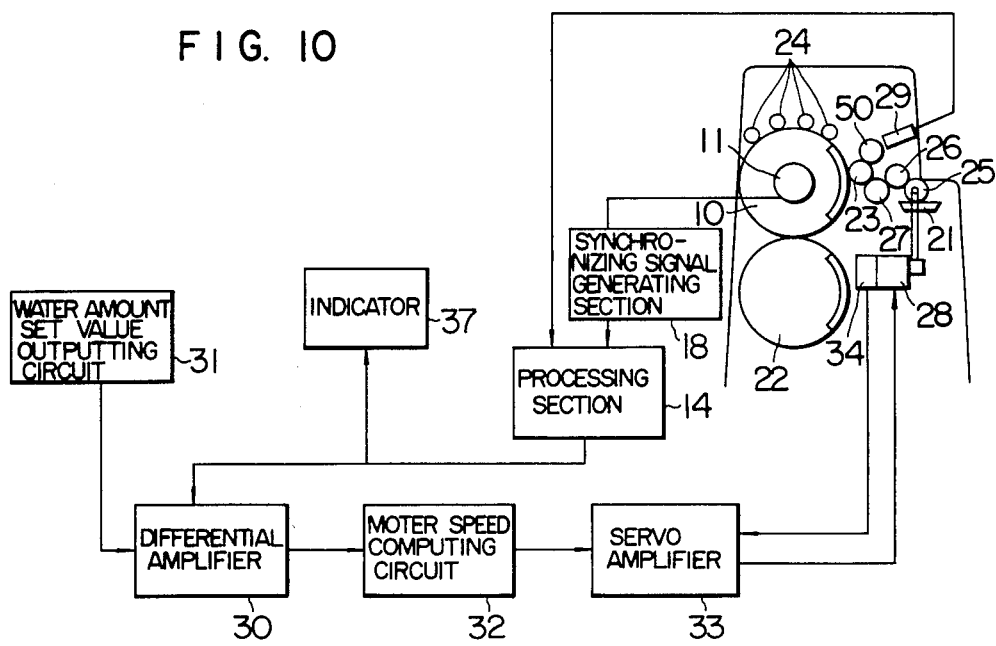
FIG. 10 is a block diagram of a dampening water supply control system employing the dampening water measuring apparatus shown in FIG. 9.
Figure 11:
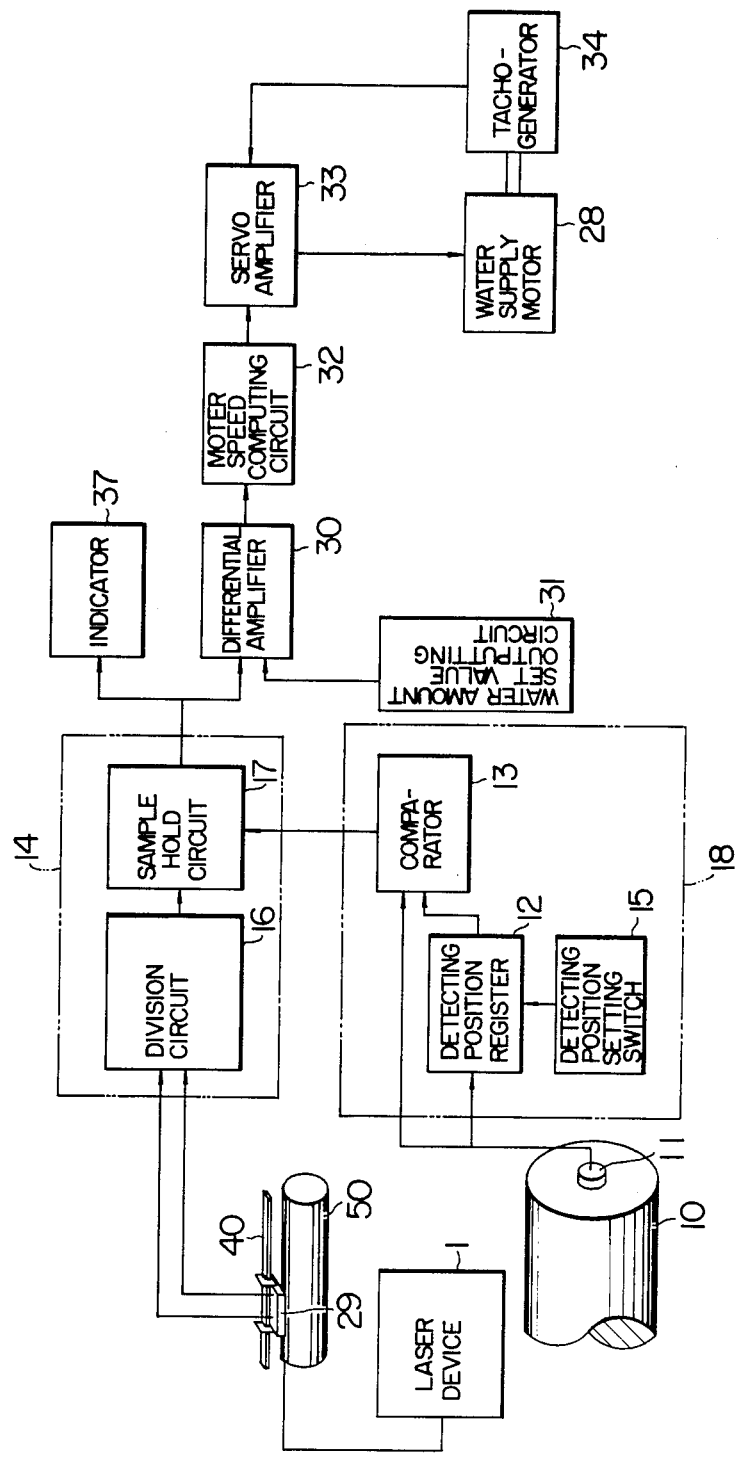
FIG. 11 is a block diagram similar to that shown in FIG. 10, but showing a part of the system in more detail.

FIG. 10 shows a dampening water control system making use of the dampening water measuring apparatus explained hereinbefore in connection with FIG. 9. The arrangement of this system is materially identical to that of the dampening water control system shown in FIG. 6 except that the sensor 29 is adapted to travel axially along the measuring roller 50 as shown in FIG. 11. No further description, therefore, will be needed as to this arrangement.

Figure 12:
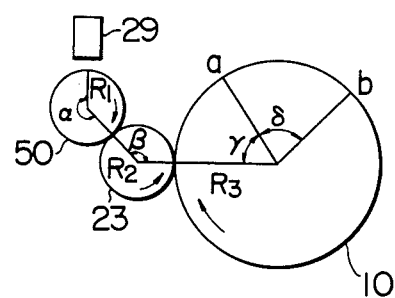
FIG. 12 is an illustration showing the relationship between the measuring position on the measuring roller and the measuring position on a plate cylinder.

FIG. 12 shows how the plate cylinder 10, dampener form roller 23, measuring roller 50 and the sensor 29 are positioned in relation to one another and how the detecting position on the measuring roler is related to the detecting position on the plate cylinder. Symbols $R_1$, $R_2$ and $R_3$ represent, respectively, radii of the measuring roller, dampener form roller and the plate cylinder, while $\alpha$ and $\beta$ represent the angle formed around the center of the measuring roller between the point of contact with the dampener form roller and the detecting position and the angle formed around the center of the dampener form roller between the point of contact with the plate cylinder and the point of contact with the measuring roller. An angle $\gamma$ is given as $\gamma = R_1\alpha + R_2\beta/R_3$. A symbol a indicates the position on the plate cylinder corresponding to the detecting position on the measuring roller.

For measuring the amount of water supplied to the plate surface, the plate cylinder is rotated to bring the detecting position to the position a, and then the sensor 29 is moved along the rail 40 shown in FIG. 11. The sensor 29, upon arriving at the position corresponding to the desired measuring position, and the detecting position memory switch 15 operates to store in the detecting position register 12 the detecting position on the measuring roller 50, i.e. the detecting position in the circumferential direction of the plate. During the measuring operation, the comparator 13 compares the output of the encoder 11, i.e. the rotational position of the cylinder 10 and the value stored in the register 12 and, when a coincidence between these two values is obtained, i.e. when the measuring roller 50 has been brought to the detecting position, the comparator 13 delivers a synchronizing signal to the sample and hold circuit 17 in the processing section 14. The sample and hold circuit 17 holds the output of the division circuit until the next synchronizing signal is received.

In this operation, the encoder 11 serves to detect the timing at which the measuring portion of the plate passes the point a shown in FIG. 12.

If the angle δ formed around the center of the plate cylinder 10 between the points b and a can be measured, it becomes possible to store the detecting position without requiring the rotation of the plate cylinder, by disposing between the encoder and the comparator a computing circuit for making a subtraction of the value corresponding to the angle 6 from the output of the encoder and inputting a signal corresponding to the angle δ to the computing circuit.

The plating cylinder 10 is adapted to be rotated in the direction of the arrow A shown in FIG. 8, so that the dampener form roller 23 and the measuring roller 50 are rotated, respectively, in the directions indicated by arrows B and C. Therefore, the balance of the water supplied to the plate surface on the plate cylinder 10, out of the water supplied from the water pan 21, is delivered to the measuring roller 50 through the dampener form roller 23. It is, therefore, possible to easily calculate the amount of the dampening water on the plate surface by measuring the amount of water on the measuring roller 50. The amount of the dampening water on the plate surface is therefore controlled and optimized by controlling the speed of the water supply motor 28 so as to eliminate the difference between the measured amount of dampening water and a reference value which is determined beforehand.

Figure 13:
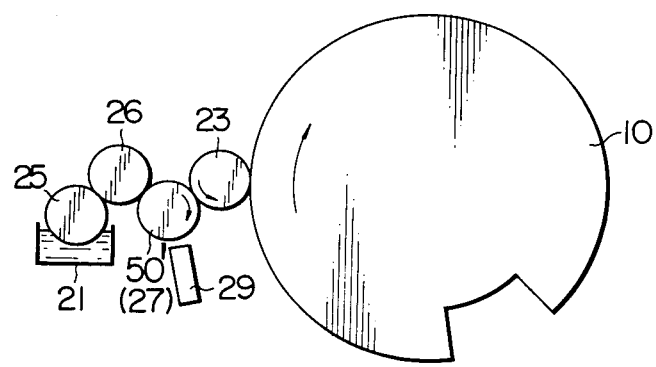
FIG. 13 is a schematic illustration of an embodiment in which one of the rollers of the dampening water supplying system is utilized as the measuring roller.

FIG. 13 shows another embodiment of the dampening water measuring apparatus of the type making use of the measuring roller. In this embodiment, unlike the preceding embodiment having an independent measuring roller separate from the rollers of the water supply system, one of rollers of the water supply system, e.g. the water transfer roller 27, is utilized also as the measuring roller 50'. In this case, the surface of the water transfer roller 27 is grained in the same way as the plate surface, and the measurement of the dampening water and the control of the supply rate of the dampening water are conducted materially in the same way as the preceding embodiment. The embodiment shown in FIG. 13 offers an advantage to save the space by eliminating the necessity for additional roller.

As has been described, the invention affords a widening of the range of measurement and reduction of the measuring error, because the dampening water is measured through sensing the mirror-reflected light which has a high directivity. In addition, it becomes possible to eliminate or suppress the influence of the roughness of the plate or roller surface and to widen the range of measurement by using a sufficiently small angle of incidence of the light.

What is claimed is:

1. A method of measuring dampening water on a printing machine comprising the steps of:

projecting parallel rays of light from a laser, at an incident angle of about 75°, onto the surface of a plate on said printing machine or onto the surface of one of a roller or rollers of a dampening water supply system through which the dampening water is supplied to the plate surface or onto the surface of a separate roller contacting one of said rollers of said water supply system;

measuring the intensity of the mirror-reflected light reflected by said surface at an angle of about 75°;

further meausring the intensity of the light diffused by said surface at an angle of 0°; and detecting the ratio between the intensity of said mirror-reflected light and the intensity of the diffused light to determine the amount of the dampening water.

2. An apparatus for measuring dampening water on a printing machine comprising:

a light projecting means for projecting parallel rays of light from a laser, at an incident angle of about 75°, onto the surface of a plate on said printing machine or onto the surface of one of rollers of a water supply system for supplying said dampening water to said plate or onto the surface of a separate roller contacting said one of said rollers of said water supply system;

a sensor adapted to receive the mirror-reflected light reflected by said surface at an angle the same as said incident angle and to measure the intensity of said mirror-reflected light, said sensor including, (a) a first photo-detecting section adapted to receive said mirror-reflected light, and (b) a first photo-electric conversion circuit connected to said first photo-detecting section;

a second sensor adapted to receive diffused light, said second sensor including;

(a) a second photo-detecting section adapted to receive a diffused light which has been reflected by said surface at an angle of 0°, and (b) a second photo-electric conversion circuit connected to said second photo-detecting section; and a division circuit for computing the ratio between the output from said first photo-electric conversion circuit and the output from said second photo-electric conversion circuit to determine the amount of the dampening water.

3. An apparatus for measuring dampening water according to claim 2, wherein said parallel rays of light are applied to the surface of a plate attached to the plate cylinder of said printing machine.

4. An appratus for measuring dampening water according to claim 2, wherein said parallel rays of light are applied to the surface of a separate roller contacting one of rollers of said water supply system, the surface of said roller to which said parallel rays of light are applied being grained.

5. An apparatus for measuring dampening water according to claim 2, wherein said parallel rays of light are applied to the surface of one of rollers of said water supply system, the surface of said roller to which said parallel rays of light are applied being grained.

* * * * *